US008509884B2

(12) United States Patent
Snyder

(10) Patent No.: US 8,509,884 B2
(45) Date of Patent: Aug. 13, 2013

(54) SYSTEMS AND METHODS TO IDENTIFY A SUBGROUP OF ADHD AT HIGHER RISK FOR COMPLICATING CONDITIONS

(75) Inventor: Steven M. Snyder, Boulder, CO (US)

(73) Assignee: Neba Health LLC, Augusta, GA (US)

(*) Notice: Subject to any disclaimer, the term of this patent is extended or adjusted under 35 U.S.C. 154(b) by 361 days.

(21) Appl. No.: 12/870,328

(22) Filed: Aug. 27, 2010

(65) Prior Publication Data
US 2011/0066065 A1 Mar. 17, 2011

Related U.S. Application Data

(60) Provisional application No. 61/237,911, filed on Aug. 28, 2009.

(51) Int. Cl.
A61B 5/04 (2006.01)

(52) U.S. Cl.
USPC ............................................ 600/544; 434/236

(58) Field of Classification Search
USPC ........................................ 600/544; 434/236
See application file for complete search history.

(56) References Cited

U.S. PATENT DOCUMENTS

| 5,083,571 A | 1/1992 | Prichep |
| 5,230,346 A | 7/1993 | Leuchter et al. |
| 5,269,315 A | 12/1993 | Leuchter et al. |
| 5,280,793 A | 1/1994 | Rosenfeld |
| 5,305,746 A | 4/1994 | Fendrock |
| 5,309,923 A | 5/1994 | Leuchter et al. |
| 5,320,109 A | 6/1994 | Chamoun et al. |

(Continued)

FOREIGN PATENT DOCUMENTS

| FR | 2070441 A | 9/1971 |
| WO | 0158351 A1 | 8/2001 |
| WO | 03057029 A2 | 7/2003 |
| WO | 2005089431 A2 | 9/2005 |

OTHER PUBLICATIONS

International Search Report and Written Opinion for PCT/US2010/046983 mailed Jan. 11, 2011.

(Continued)

Primary Examiner — Patricia Mallari
Assistant Examiner — Etsub Berhanu
(74) Attorney, Agent, or Firm — Duft Bornsen & Fettig LLP

(57) ABSTRACT

This invention is directed to embodiments of systems and methods to identify a subgroup of ADHD at higher risk for complicating conditions that, for example, may be of concern to an ADHD evaluation, may account for attention and behavior symptoms, and may lead a clinician to exclusion of ADHD from primary diagnosis. In one embodiment, a method for identifying a subgroup of attention deficit hyperactivity disorder (ADHD) patients at higher risk for complicating conditions is provided. The method can include receiving, from a user or clinician, evaluation data associated with a plurality of patients identified with ADHD as a primary diagnosis; obtaining EEG data for each of the plurality of patients; determining, based at least in part on the EEG data, an indicator of ADHD, wherein the indicator supports a positive or negative ADHD evaluation; correlating the indicator with a user's or clinician's evaluation data; and based at least in part on the correlation, determining at least one subgroup of the plurality of patients, wherein the correlation provides positive support for diagnosis of ADHD or provides support for further testing for complicating conditions before proceeding with diagnosis of ADHD in at least one patient within the at least one subgroup.

20 Claims, 11 Drawing Sheets

(56) References Cited

U.S. PATENT DOCUMENTS

| | | | |
|---|---|---|---|
| 5,368,041 | A | 11/1994 | Shambroom |
| 5,381,804 | A | 1/1995 | Shambroom |
| 5,450,855 | A | 9/1995 | Rosenfeld |
| 5,458,117 | A | 10/1995 | Chamoun et al. |
| 5,564,433 | A | 10/1996 | Thornton |
| 5,792,069 | A | 8/1998 | Greenwald et al. |
| 5,813,404 | A | 9/1998 | Devlin et al. |
| 6,032,064 | A | 2/2000 | Devlin et al. |
| 6,032,072 | A | 2/2000 | Greenwald et al. |
| 6,052,619 | A | 4/2000 | John |
| 6,097,980 | A | 8/2000 | Monastra et al. |
| 6,236,874 | B1 | 5/2001 | Devlin et al. |
| 6,298,255 | B1 | 10/2001 | Cordero et al. |
| 6,338,713 | B1 | 1/2002 | Chamoun et al. |
| 6,394,953 | B1 | 5/2002 | Devlin et al. |
| 6,434,410 | B1 | 8/2002 | Cordero et al. |
| 6,488,617 | B1 | 12/2002 | Katz |
| 6,599,281 | B1 | 7/2003 | Struys et al. |
| 6,605,072 | B2 | 8/2003 | Struys et al. |
| 6,654,626 | B2 | 11/2003 | Devlin et al. |
| 6,882,166 | B2 | 4/2005 | Shambroom et al. |
| 2003/0135128 | A1 | 7/2003 | Suffin et al. |
| 2004/0152995 | A1 | 8/2004 | Cox et al. |
| 2007/0100251 | A1 | 5/2007 | Prichep |
| 2007/0197882 | A1* | 8/2007 | Smith et al. .................... 600/300 |
| 2008/0269632 | A1* | 10/2008 | Snyder .......................... 600/544 |

OTHER PUBLICATIONS

Robert J. Barry et al. "Electroenceohalogram Ratio and Arousal in Attention-Deficit/Hyperactivity Disorder: Evidence of Independent Processes." Biological Psychiatry. Aug. 15, 2009, vol. 66, No. 4. 398-401.

S. Koehler et al. "Increased EEG Power Density in Alpha and Theta Bands in Adult ADHD Patients." Journal of Neural Transmission. Nov. 22, 2008, vol. 116, No. 1. 97-104.

Almkvist et al. "Early Diagnosis of Alzheimer Dementia Based on Clinical and Biological Factors." Eur Arch Psychiatry Clin Neurosci (1999) 249: Suppl. 3 III/3-III/9.

van der Flier et al. "Epidemiology and Risk Factors of Dementia." J. Neurol. Neurosurg. Psychiatry 2005. 76; v2-v7.

Qiu et al. "Heart Failure and Risk of Dementia and Alzheimer Disease." Arch Intern Med. 2006. 166: 1003-1008.

Luchsinger et al. "Aggregation of Vascular Risk Factors and Risk of Incident Alzheimer's Disease." Neurology. Aug. 23, 2005, vol. 65, No. 4. 545-551.

Leuchter, Andrew. "Aspect Neuroscience Actively Developing Significant Applications for its Brain Assessment Technology." Insight—Aspect Medical Systems Newsletter. Fall 2004.

James A. Coan et al. "Frontal EEG Asymmetry as a Moderator and Mediator of Emotion." Oct. 2004, vol. 67, No. 1-2. 7-49.

H. H. Stassen et al. "Genetic Determination of the Human EEG." Hum Genet (1998), vol. 80. 165-176.

John J. B. Allen et al. "Frontal EEG Assymetry, Emotion, and Psychopathology: The First, and the Next 25 Years." J. Biological Psychology. 2004, vol. 67. 1-5.

Elsa Baehr et al. "Comparison of Two EEG Asymmetry Indices in Depressed Patients vs. Normal Controls." International Journal of Psychopsychology. 1998, vol. 31. 89-92.

Elsa Baehr et al. "Premenstrual Dysphoric Disorder and Changes in Frontal Alpha Asymmetry." International Journal of Psychophysiology. 2004, vol. 52. 159-167.

Davidson, Richard. "Anterior Electrophysiological Asymmetries, Emotion, and Depression: Conceptual and Methodological Conundrums." Psychophysiology. 1998, vol. 35. 607-614.

La Vague, T. "Living Things, Control Systems, and Biofeedback." 2002 (http://www.biofeedbackcalifornia.org/Uploads/Past_Issues/BSC_Summer_2002.pdf>.

"Playing Catch Up: Mind Over Matter and More." Innovations Publishing, LLC. Oct. 1, 2002 <http://www.innovationspublishing.com/georgia/loadArticle.asp?id=60>.

Lombardo, T. "Company Says Brain Scan Can Help Diagnose Disorder." August Chronicle. Mar. 23, 2006 <http://chronicle.augusta.com/stories/032306/bus_6846478.shtml>.

International Search Report and Written Opinion for PCT/US2007/082266 mailed May 29, 2008.

Quintana, H. "Comparison of a Standard Psychiatric Evaluation to Rating Scales and EEG in the Differential Diagnosis of Attention-Deficit/Hyperactivity Disorder." Science Direct. Apr. 22, 2005, vol. 152. 211-222.

S. Snyder et al. "Review of Clinical Validation of ADHD Behavior Rating Scales." Psychological Reports. Aug. 14, 2006, vol. 99. 363-378.

S. Snyder et al. "A Meta-Analysis of Quantitative EEG Power Associated with Attention-Deficit Hyperactivity Disorder." Journal of Clinical Psychology. Oct. 23, 2006, vol. 23. 441-456.

International Search Report and Written Opinion for PCT/US2007/071789 mailed Jun. 13, 2008.

Barry et al. "A Review of Electrophysiology in Attention-Deficit/Hyperactivity Disorder: I. Qualitative and Quantitative Electroencephalography." Clinical Neurophysiology. Sep. 24, 2004, vol. 114. 171-183.

* cited by examiner

|   | | System Result | | |
|---|---|---|---|---|
|   | | Negative | Uncertain | Positive |
| Clinician's ADHD Evaluation | Positive | Strongly Recommend Further Clinical Testing. | Suggest Further Clinical Testing. | Confirmatory Support. |
|   | Uncertain | Strongly Recommend Further Clinical Testing. | Suggest Further Clinical Testing. | Suggest Further Clinical Testing. |
|   | Negative | Confirmatory Support. | Negative. Review other possibilities for TBR increase. | Negative. Review other possibilities for TBR increase. |

FIG. 3

| Clinician's ADHD Evaluation | NEBA™ Result | Interpretation |
|---|---|---|
| Positive | Positive | Confirmatory support for presence of ADHD. Suggest using EEG as part of discussion with patient on biological aspects of ADHD. |
| Positive | Uncertain | *Suggest* further clinical testing with *focus on ruling in/out other conditions* before proceeding with ADHD as primary diagnosis. |
| Positive | Negative | *Strongly recommend* further clinical testing with *focus on ruling in/out other conditions* before proceeding with ADHD as primary diagnosis. |
| Uncertain | Positive | *Suggest* further clinical testing with *focus on ruling in/out ADHD* before considering other disorders for primary diagnosis. |
| Uncertain | Uncertain | *Suggest* further clinical testing with *focus on ruling in/out other conditions* before considering ADHD as a possible primary diagnosis. |
| Uncertain | Negative | *Strongly recommend* further clinical testing with *focus on ruling in/out other conditions* before considering ADHD as a possible primary diagnosis. |
| Negative | Positive | Negative. No ADHD diagnosis is possible without the clinician's determination of ADHD DSM-IV criteria. Suggest reviewing other possibilities for elevated theta/beta ratio. |
| Negative | Uncertain | Negative. No ADHD diagnosis is possible without the clinician's determination of ADHD DSM-IV criteria. Suggest reviewing other possibilities for slightly elevated theta/beta ratio. |
| Negative | Negative | Confirmatory support for absence of ADHD. Suggest using EEG as part of discussion with patient on biological aspects of disorders. |

FIG. 4

Evaluation of the NEBA system per the *intended use*

| NEBA Interpretation Guidelines | | | Evaluation in the Clinical Investigation | | |
|---|---|---|---|---|---|
| Clinician's ADHD Evaluation | NEBA Result | NEBA Interpretation | TRUE | FALSE | Analysis |
| Positive | Positive | Confirmatory support for presence of ADHD. | ADHD=yes EEG=yes | ADHD=no EEG=yes (for analysis)* | PPV |
| Positive | Uncertain (equivocal) | Suggest further clinical testing with focus on ruling in/out other conditions before proceeding with ADHD as primary diagnosis. | ADHD=yes EEG=equivocal Complications=no | ADHD=yes EEG=equivocal Complications=no | NPV OR (Complications) |
| Positive | Negative | Strongly recommend further clinical testing with focus on ruling in/out other conditions before proceeding with ADHD as primary diagnosis. | ADHD=yes EEG=no Complications=yes | ADHD=yes EEG=no Complications=no | NPV OR (Complications) |
| Uncertain (ambiguous) | Positive | Suggest further clinical testing with focus on ruling in/out ADHD before considering other disorders for primary diagnosis. | n/a (outcome unknown in study) | n/a (outcome unknown in study) | n/a (outcome unknown in study) |
| Uncertain (ambiguous) | Uncertain (equivocal) | Suggest further clinical testing with focus on ruling in/out other conditions before considering ADHD as a possible primary diagnosis. | ADHD=ambiguous EEG=equivocal Complications=no | ADHD=ambiguous EEG=equivocal Complications=no | NPV OR (Complications) |
| Uncertain (ambiguous) | Negative | Strongly recommend further clinical testing with focus on ruling in/out other conditions before considering ADHD as a possible primary diagnosis. | ADHD=ambiguous EEG=no Complications=yes | ADHD=ambiguous EEG=no Complications=no | NPV OR (Complications) |

*For the purpose of analysis, ADHD-negative / NEBA-positive results were included as false answers; ADHD-negative / NEBA-negative, and ADHD-negative / EEG-equivocal results were included as true answers. However by the intended use, these results would all be true answers because the clinician's negative evaluation would always take precedence in the NEBA interpretation: "No ADHD diagnosis is possible without the clinician's determination of ADHD DSM-IV criteria."

| Group | n | Sensitivity, % (CI) | Specificity, % (CI) | Positive Predictive Value, % (CI) | Negative Predictive Value, % (CI) |
|---|---|---|---|---|---|
| Adolescents | 68 | 90 (83-97) | 97 (94-100) | 96 (92-100) | 93 (86-99) |
| Children | 192 | 73 (66-81) | 94 (90-97) | 93 (89-96) | 78 (72-84) |
| Total | 260 | 78 (73-83) | 95 (92-97) | 94 (91-97) | 82 (77-86) | n= sample size, CI = 95% confidence interval

FIG. 8

| Category | Subgroup | n | Overall Accuracy, % |
|---|---|---|---|
| Age | 6-11 years | 192 | 84 |
| Age | 12-17 years | 68 | 94 |
| Gender | Female | 167 | 87 |
| Gender | Male | 91 | 86 |
| Race | White | 184 | 88 |
| Race | Non-white | 69 | 84 |
| SES | Uppermiddle | 129 | 89 |
| SES | Working/Lower | 131 | 84 |
| Total | | 260 | 87 | n= sample size, SES= socioeconomic status

| Disorder | Presence in Subgroup | n | Overall Accuracy, % |
|---|---|---|---|
| An Anxiety Disorder | present | 49 | 90 |
| An Anxiety Disorder | absent | 211 | 86 |
| A Mood Disorder | present | 25 | 92 |
| A Mood Disorder | absent | 235 | 86 |
| A Disruptive Disorder | present | 85 | 99 |
| A Disruptive Disorder | absent | 175 | 83 |
| A Learning Disorder | present | 94 | 90 |
| A Learning Disorder | absent | 166 | 84 |
| Total | | 260 | 87 | n= sample size

FIG. 9

| Site # | Site Type | Sector | US Region | n | Overall Accuracy, % |
|---|---|---|---|---|---|
| 1 | Psychiatry | Academic | South | 17 | 82 |
| 2 | Pediatrics | Private | West | 25 | 88 |
| 3 | Pediatrics | Private | Northeast | 18 | 89 |
| 4 | Psychiatry | Academic | Northeast | 18 | 83 |
| 5 | Psychology | Academic | South | 18 | 89 |
| 6 | Psychology | Academic | South | 28 | 100 |
| 7 | Psychology | Private | South | 26 | 88 |
| 8 | Pediatrics | Private | South | 22 | 73 |
| 9 | Psychiatry | Private | Midwest | 18 | 89 |
| 10 | Pediatrics | Academic | South | 16 | 81 |
| 11 | Pediatrics | Private | Northeast | 12 | 92 |
| 12 | Psychiatry | Private | Midwest | 23 | 83 |
| 13 | Psychiatry | Private | South | 19 | 84 |
| Total | | | | 260 | 87 | n= sample size

FIG. 10

SYSTEMS AND METHODS TO IDENTIFY A SUBGROUP OF ADHD AT HIGHER RISK FOR COMPLICATING CONDITIONS

RELATED APPLICATION

This application claims priority to U.S. Ser. No. 61/237,911, entitled "Systems and Methods to Identify a Subgroup of ADHD at Higher Risk for Complicating Conditions," filed Aug. 28, 2009, the contents of which are hereby incorporated by reference.

FIELD OF THE INVENTION

The invention relates to detection of biological disorders, and relates more particularly to systems and methods to identify a subgroup of ADHD at higher risk for complicating conditions.

BACKGROUND OF THE INVENTION

The American Psychiatric Association (APA) publishes the Diagnostic and Statistical Manual of Mental Disorders (the current version is the DSM-IV-Text Revision). The DSM-IV provides definitions and criteria that support a clinician's diagnosis of mental disorders. The DSM-IV provides the generally accepted criteria for defining ADHD (attention-deficit/hyperactivity disorder). ADHD is characterized by DSM-IV criteria in part by presence of certain attention and behavior symptoms. Additionally, the DSM-IV criteria require that the symptoms are not better accounted for by another disorder. As such, ADHD evaluation can be relatively complicated because ADHD-like symptoms are known to be present in other psychiatric disorders, as well as in medical and neurological conditions. For instance, the DSM-IV criteria for depression include psychomotor agitation/restlessness, difficulty making decisions, and difficulty concentrating. The DSM-IV criteria for mania include excessive talking, racing thoughts, distractibility, and psychomotor agitation/restlessness. The DSM-IV criteria for anxiety disorder include concentration difficulties. There are also a number of medical mimics of ADHD including anemia, hearing or vision loss, congenital brain anomalies, mental retardation, medication effects, and head injury (Pearl et al., 2001). Thus, a need exists for an ADHD assessment aid that can effectively or otherwise suitably support separation of attention and behavior symptoms due to ADHD from those due to other conditions.

ADHD behavior rating scales are assessment tools that are recommended in the support of ADHD diagnosis in professional guidelines such as those from the American Academy of Pediatrics (AAP, 2000). The rating scales are designed to assist in the recognition of the attention and behavior symptoms of ADHD as defined by the DSM-IV. However, it is commonly known that attention and behavior symptoms of ADHD are present with other disorders as well as medical and neurological conditions. In addition, many of these common disorders are comorbid in up to 67% of ADHD cases (Cantwell, 1996; Wolraich et al., 1998). Therefore in an ADHD diagnostic evaluation, a clinician faces the challenge of determining whether ADHD is the primary cause of the symptoms, whether the ADHD symptoms are secondary to other diagnoses, or whether ADHD is comorbid with other diagnoses (APA, 1994; Cantwell, 1996; Zametkin and Ernst, 1999). Therefore, a need still exists for an ADHD assessment aid that can effectively or otherwise suitably support separation of attention and behavior symptoms due to ADHD from those due to other conditions.

Professional guidelines have been developed to assist in the implementation of DSM-IV criteria in ADHD diagnosis using evidence such as that from assessment tools. EEG (electroencephalography) is not currently listed in the DSM-IV criteria for ADHD. There is no known mention of using EEG with any guidelines that support the implementation of DSM-IV criteria in ADHD diagnosis such as the guidelines from the American Academy of Pediatrics (AAP, 2000).

At least one conventional technique uses EEG data to diagnose ADHD using an assessment of EEG data collected from a patient. One conventional technique determines a ratio between digitized EEG data in the theta (4-8 Hz) and beta (13-21 Hz) frequency ranges collected from a patient. EEG data is collected from the patient during baseline and at least three attentive behavior tasks. An overall index is calculated for the patient using the ratios determined during the baseline and at least three attentive behavior tasks. The overall index is finally compared to a non-clinical database of normal individuals without ADHD or any neurological disorder to determine the presence and severity of the patient's ADHD. However, the conventional technique is limited to diagnosing ADHD in a patient, and does not address differentiating among ADHD patients diagnosed by a clinician. Furthermore, the conventional technique is a stand-alone diagnostic that does not support the implementation of DSM-IV criteria. Furthermore, the conventional technique does not address the DSM-IV criterion that requires that attention and behavior symptoms in a patient are not better accounted for by another condition. Finally, the conventional technique does not address whether attention and behavior symptoms in a patient are more likely to be due to ADHD or due to another condition. Therefore, a need still exists for an ADHD assessment aid that can effectively or otherwise suitably support separation of attention and behavior symptoms due to ADHD from those due to other conditions.

At least one conventional technique uses EEG data to diagnose disorders of impaired attention using an assessment of EEG data collected from a patient. One conventional technique determines differences between EEG parameters collected from a patient during at least two tasks. An overall index is calculated for the patient using the absolute value of the sum of the EEG differences between tasks by distance. The overall index is finally compared to a non-clinical database of normal individuals without psychiatric disorders to determine the presence of a disorder with impaired attention such as ADHD. However, the conventional technique is limited to diagnosing attention disorders in a patient, and does not address differentiating among ADHD patients diagnosed by a clinician. Furthermore, the conventional technique does not address the DSM-IV criterion that requires that attention and behavior symptoms in a patient are not better accounted for by another condition. Finally, the conventional technique does not address whether attention and behavior symptoms in a patient are more likely to be due to ADHD or due to another condition. Therefore, a need still exists for an ADHD assessment aid that can effectively or otherwise suitably support separation of attention and behavior symptoms due to ADHD from those due to other conditions.

SUMMARY OF THE INVENTION

Certain embodiments of the invention can use systems and methods to identify a subgroup of attention deficit hyperactivity disorder (ADHD) patients at higher risk for complicating conditions that, for example, may be of concern to an ADHD evaluation, may account for attention and behavior symptoms, and may lead a clinician to exclusion of ADHD from primary diagnosis. In one embodiment, EEG data is used to separate patients already diagnosed with ADHD into at least two subgroups having clinical differences that are relevant to a clinician's ADHD evaluation. In certain embodiments, one or more predefined cutoffs or thresholds can be applied to the EEG data to determine at least two subgroups having clinical differences that are relevant to a clinician's ADHD evaluation. In certain embodiments, a clinical database of patients with attention and behavior symptoms but not all with ADHD can be applied to the EEG data to determine at least two subgroups having clinical differences that are relevant to a clinician's ADHD evaluation. In certain other embodiments, using EEG data recorded under simple baseline conditions for each of a plurality of patients, the EEG data can be used to determine at least two subgroups having clinical differences that are relevant to a clinician's evaluation. In certain embodiments, EEG data is used to separate patients already diagnosed with ADHD into at least two subgroups with clinical differences that support addressing the DSM-IV criterion that requires that attention and behavior symptoms in a patient are not better accounted for by another condition. In certain embodiments, EEG data is used to separate patients already diagnosed with ADHD into at least two subgroups with clinical differences that support determining whether attention and behavior symptoms in a patient are more likely to be due to ADHD or due to another condition. In certain embodiments, EEG data is used to separate patients already diagnosed with ADHD into at least two subgroups with clinical differences that can effectively or otherwise suitably support separation of attention and behavior symptoms due to ADHD from those due to other conditions.

In one embodiment, a system for identifying a subgroup of ADHD patients at higher risk for complicating conditions can be provided. The system can include a data collection module operable to receive, from a user or clinician, evaluation data associated with a plurality of patients identified with ADHD as a primary diagnosis. The data collection module can be further operable to obtain EEG data for each of the plurality of patients. The system can further include a clinical/diagnostic module operable to determine, based at least in part on the EEG data, an indicator of ADHD, wherein the indicator supports a positive or negative ADHD evaluation. The system can also include a subgroup identification module operable to correlate the indicator with the user's or clinician's evaluation data, and to determine at least one subgroup of the plurality of patients based at least in part on the correlation, wherein the correlation provides positive support for diagnosis of ADHD or provides support for further testing for complicating conditions before proceeding with diagnosis of ADHD in at least one patient within the at least one subgroup.

In another embodiment, a computer program product is provided. The computer program product can include a computer readable medium having computer readable code adapted to be executed to implement a method for identifying a subgroup of ADHD patients at higher risk for complicating conditions. The method can include providing a system, wherein the system comprises a plurality of software modules, wherein the plurality of software modules comprises a data collection module, a clinical/diagnostic module, a subgroup identification module, and optionally a report module. The method can further include receiving, from a user or clinician, evaluation data associated with a plurality of patients identified with ADHD as a primary diagnosis. The method can also include obtaining, via the data collection module, EEG data for each of the plurality of patients. The method can further include determining, based at least in part on the EEG data, an indicator of ADHD, wherein the EEG data supports a positive or negative ADHD evaluation. Further, the method can include determining, via the subgroup identification module, at least one subgroup of the plurality of patients based at least in part on the correlation, wherein the correlation provides positive or negative support for diagnosis of ADHD in at least one patient within the at least one subgroup.

In yet another embodiment, a method for identifying a subgroup of ADHD patients at risk for complicating conditions is provided. The method can include receiving, from a user or clinician, evaluation data associated with a plurality of patients identified with ADHD as a primary diagnosis; obtaining EEG data for each of the plurality of patients; based at least in part on the EEG data, determining an indicator of ADHD, wherein the indicator supports a positive or negative ADHD evaluation; and based at least in part on the correlation, determining at least one subgroup of the plurality of patients, wherein the correlation provides positive support for diagnosis of ADHD or provides support for further testing for complicating conditions before proceeding with diagnosis of ADHD in at least one patient within the at least one subgroup.

Certain embodiments of the invention can use standardized EEG results to separate a previously diagnosed ADHD group into at least two subgroups, (1) a subgroup receiving confirmatory support, "CS", and (2) a subgroup receiving a recommendation for further testing, "FT". Certain embodiments of the invention can also facilitate increased clinical value because the FT and CS subgroups have significant differences in clinical characteristics that are meaningful to a user or clinician's evaluation. Furthermore, certain embodiments of the invention can use EEG results to separate a group of ADHD patients into clinically meaningful subgroups.

Certain embodiments of the invention can support the integration of EEG into a clinical setting, to detect a subgroup of ADHD that is at higher risk for conditions that would be of concern to an ADHD evaluation, to provide recommendation for further testing in a subgroup of ADHD that is more likely to have complicating conditions, to detect a subgroup of ADHD that is at lower risk for conditions that would be of concern to an ADHD evaluation, and to provide confirmatory support of a user's or clinician's ADHD evaluation, or other ADHD evaluation in a subgroup of ADHD that is less likely to have complicating conditions.

Other embodiments, aspects, and features of the invention will become apparent from the following detailed description, the accompanying drawings, and the appended claims.

BRIEF DESCRIPTION OF THE DRAWINGS

The foregoing, and other embodiments, aspects, and feature will be better understood from the following detailed description of the certain embodiments of the invention with reference to the drawings, in which:

FIG. 3 illustrates example interpretations for correlating an ADHD evaluation with a system result in accordance with an embodiment of the invention.

FIG. 4 illustrates example interpretations when correlating an ADHD evaluation with a system result in accordance with an embodiment of the invention.

FIG. 6 illustrates example interpretation guidelines in accordance with an embodiment of the invention.

FIGS. 7-10 illustrate various statistical clinical support in the form of accuracy results for an example implementation of an embodiment of the invention.

DETAILED DESCRIPTION OF VARIOUS EMBODIMENTS

Illustrative embodiments of the invention now will be described more fully hereinafter with reference to the accompanying drawings, in which example embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Certain embodiments of the invention can use systems and methods to identify a subgroup of ADHD at higher risk for complicating conditions that, for example, would be of concern to an ADHD evaluation, may account for attention and behavior symptoms, and may lead a clinician to exclusion of ADHD from primary diagnosis. Certain embodiments of the invention can use EEG analysis and interpretation to separate a previously diagnosed ADHD group into, for instance, at least two clinically meaningful subgroups: (1) a subgroup receiving confirmatory support for a clinician's ADHD evaluation, and (2) a subgroup receiving a recommendation for further clinical testing of other conditions before proceeding with ADHD as primary diagnosis. Certain study results support the observation that there can be significant clinical differences in these two subgroups that would be of concern to a clinician conducting an ADHD evaluation. The clinical differences between subgroups can include risk of complicating conditions that could account for ADHD symptoms. The subgroup receiving confirmatory support is less likely to have complicating conditions that could account for ADHD symptoms. The subgroup receiving a recommendation for further clinical testing is more likely to have complicating conditions that could account for ADHD symptoms. Therefore, one technical effect of certain embodiments of the invention is to separate a previously diagnosed ADHD group into at least two clinically meaningful subgroups, which solves the prior technical problem of being unable to distinguish among patients in a previously diagnosed ADHD group, and addresses the need for an ADHD assessment aid that can effectively or otherwise suitably support separation of attention and behavior symptoms due to ADHD from those due to other conditions.

Figure 1:
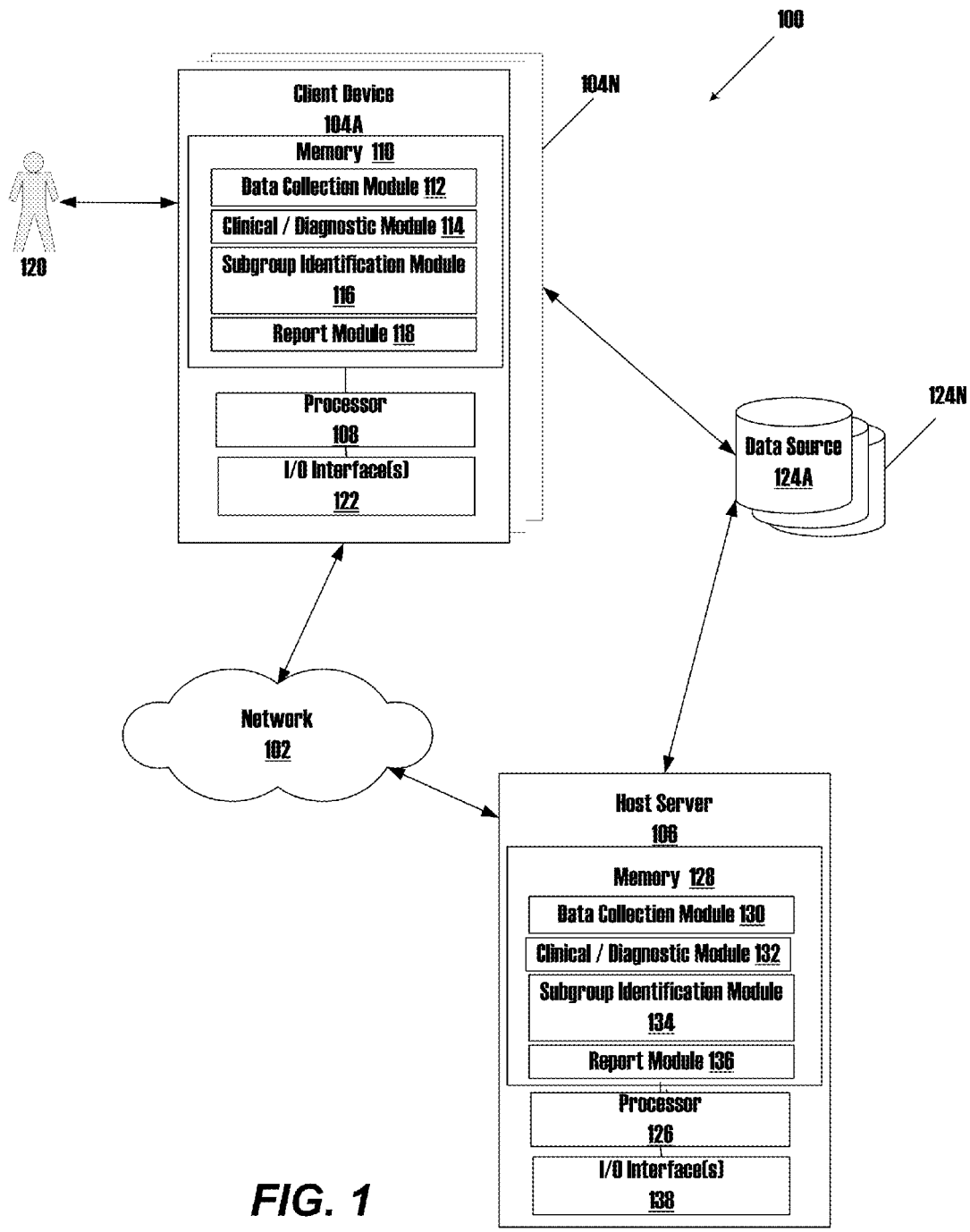
FIG. 1 illustrates an example environment and system in accordance with an embodiment of the invention.

FIG. 1 illustrates an example environment and system 100 in accordance with an embodiment of the invention. Using a system 100 illustrated in FIG. 1, various methods for identifying a subgroup of ADHD patients at higher risk for complicating conditions in accordance with embodiments of the invention can be performed. In one example, the processes embodied in FIGS. 3, 4 and 5 can be implemented with the system 100 shown in FIG. 1. Other systems in accordance with other embodiments of the invention can include similar system components as shown in FIG. 1, or other components, elements, and modules.

In the example shown in FIG. 1, the environment can be a client-server configuration, and the system 100 can be a subgroup identification system. The system 100 is shown with a communications network 102, such as the Internet, in communication with at least one client device 104A. Any number of other client devices 104N can also be in communication with the network 102. In any instance, each of the client devices 104A-104N can be operable to receive information from at least one patient or user. The network 102 is also shown in communication with at least one server 106, such as a website host server. Any number of other servers or website host servers can also be in communication with the network 102.

The communications network 102 shown in FIG. 1 can be, for example, the Internet. In another embodiment, the network 102 can be a wireless communications network capable of transmitting both voice and data signals, including image data signals or multimedia signals. Other types of communications networks, including local area networks (LAN), wide area networks (WAN), a public switched telephone network, or combinations thereof can be used in accordance with various embodiments of the invention.

Each client device 104A-104N can be a computer or processor-based device capable of communicating with the communications network 102 via a signal, such as a wireless frequency signal or a direct wired communication signal. A respective communication or input/output interface 120 associated with each client device 104A-104N can facilitate communications between the client device 104A-104N and the network 102 or Internet. Each client device, such as 104A, can include a processor 108 and a computer-readable medium, such as a random access memory (RAM) 110, coupled to the processor 108. The processor 108 can execute computer-executable program instructions stored in memory 110. In some embodiments, the computer executable program instructions stored in memory 110 can include an Internet browser application program. The Internet browser application program can be adapted to access and/or receive one or more webpages and associated content from at least one remotely located server, such as 106, or website host server. The computer executable program instructions stored in memory 110 can also include a data collection module or application program, such as 112; a clinical/diagnostic module or application program, such as 114; a subgroup identification module or application program, such as 116; and optionally a report module or application program, such as 118. The data collection module 112 can be adapted to access and/or receive EEG or biological data from a biological data collector or EEG collection device in communication with a patient, or a from a client device, such as 104A, via a network, such as 102. EEG or biological data can be received in real-time or near-realtime, or may be previously stored from a prior data collection session. The data collection module 112 can further be adapted to receive, from a user or clinician, evaluation data associated with a plurality of patients identified with ADHD as a primary diagnosis. In certain embodiments, the data collection module 112 also can be adapted to identify a plurality of patients having ADHD as a primary diagnosis. For example, using an online questionnaire or series of questions designed to elicit patient information associated with diagnosing ADHD in the patient, a data collection module such as 112 can receive responses from the patient and/or other suitable informant(s). Based at least in part on the responses from the patient and/or other suitable informant(s), the data collection module 112 can identify a plurality of patients having ADHD as a primary diagnosis.

The clinical/diagnostic module 114 can be adapted to, based at least in part on the EEG or biological data, determine an indicator of ADHD, wherein the indicator supports a positive or negative ADHD evaluation.

The subgroup identification module 116 can be adapted to correlate the indicator with the user's or clinician's evaluation data. Further, the subgroup identification module 116 can be adapted to, based at least in part on the correlation, determine at least one subgroup of the plurality of patients, wherein the correlation provides positive support for diagnosis of ADHD or provides support for further testing for complicating conditions before proceeding with diagnosis of ADHD in at least one patient within the at least one subgroup.

The optional report module 118 can be adapted to output an indication for at least one patient within the at least one subgroup, wherein the indication corresponds to whether the correlation provides positive support for diagnosis of ADHD or provides support for further testing for complicating conditions before proceeding with diagnosis of ADHD in the at least one patient.

In one embodiment, the computer executable program instructions stored in memory 110 and associated functionality facilitated by modules 112, 114, 116, and 118 can be implemented by a NEBA™ (neuropsychiatric EEG-based assessment aid for ADHD) system, provided by Lexicor Medical Technology, Inc.

The server 106 can be a computer or processor-based device capable of communicating with the communications network 102 via a signal, such as a wireless frequency signal or a direct wired communication signal. Server 106, depicted as a single computer system, may be implemented as a network of computer processors. Examples of suitable servers are server devices, mainframe computers, networked computers, a processor-based device, and similar types of systems and devices. The server, such as 106, can include a processor 126 and a computer-readable medium, such as a random access memory (RAM) 128, coupled to the processor 126. The processor 124 can execute computer-executable program instructions stored in memory 128. In some embodiments, the computer executable program instructions stored in memory 128 can include a website server application program. The website server application program can be adapted to transmit one or more webpages and any associated content from the server 106. Similar to the computer executable program instructions above in the client devices 104A-104N, the computer executable program instructions stored in memory 128 can also include a data collection module or application program, such as 130; a clinical/diagnostic module or application program, such as 132; a subgroup identification module or application program, such as 134; and optionally a report module or application program, such as 136. The data collection module 130 can be adapted to access and/or receive EEG or biological data from a biological data collector or EEG collection device in communication with a patient, or from a client device, such as 104A, via a network, such as 102. EEG or biological data can be received in realtime or near-realtime, or may be previously stored from a prior data collection session. The data collection module 130 can further be adapted to receive, from a user or clinician, evaluation data associated with a plurality of patients identified with ADHD as a primary diagnosis. In certain embodiments, the data collection module 130 can be adapted to identify a plurality of patients having ADHD as a primary diagnosis. For example, using an online questionnaire or series of questions designed to elicit patient information associated with diagnosing ADHD in the patient, a data collection module such as 130 can receive responses from the patient and/or other suitable informant(s). Based at least in part on the responses from the patient and/or suitable informant(s), the data collection module 130 can identify a plurality of patients having ADHD as a primary diagnosis. The clinical/diagnostic module 132 can be adapted to, based at least in part on the EEG or biological data, determine an indicator of ADHD, wherein the indicator supports a positive or negative ADHD evaluation. The subgroup identification module 134 can be adapted to correlate the indicator with the user's or clinician's evaluation data. Further, the subgroup identification module 134 can be adapted to, based at least in part on the correlation, determine at least one subgroup of the plurality of patients, wherein the correlation provides positive support for diagnosis of ADHD or provides support for further testing for complicating conditions before proceeding with diagnosis of ADHD in at least one patient within the at least one subgroup. The optional report module 136 can be adapted to output an indication for at least one patient within the at least one subgroup, wherein the indication corresponds to whether the correlation provides positive support for diagnosis of ADHD or provides support for further testing for complicating conditions before proceeding with diagnosis of ADHD in the at least one patient.

A user, such as 120, can be a person associated with a health care entity, or a researcher. In either instance, the user can operate a computer or processor-based device capable of communicating with the communications network 102 via a signal, such as a wireless frequency signal or a direct wired communication signal. In at least one embodiment, more than one user, such as 120, can be in communication with a respective client device 104A-104N.

A data collection module, such as 112 and 130, can be adapted to receive and/or collect various biological or EEG data from any number of client devices 104A-104N, EEG data collection devices, and/or servers 106. The data collection module, such as 112 and 130, can also be adapted to identify one or more patients having ADHD as a primary diagnosis. In one embodiment, a data collection module can include computer code operable to receive and/or collect various biological or EEG data from any number of client devices 104A-104N, EEG data collection devices, and/or servers 108. Furthermore, a data collection module can include computer code operable to identify one or more patients having ADHD as a primary diagnosis. The data collection module 112 can include additional computer code operable to receive, from a user or clinician, evaluation data associated with a plurality of patients identified with ADHD as a primary diagnosis.

A clinical/diagnostic module, such as 114 and 132, can be adapted to receive and/or collect a clinical evaluation for one or more patients from at least one clinician or other health care professional. In one embodiment, a clinical/diagnostic module can include computer code operable to receive and/or collect a clinical evaluation for one or more patients from at least one clinician or other health care professional. In another instance, a clinical/diagnostic module can be adapted to support, based at least in part on received EEG or biological data, at least one clinical evaluation for one or more patients. In one embodiment, a clinical/diagnostic module can include computer code operable to support, based at least in part on received EEG or biological data, at least one clinical evaluation for one or more patients. In any instance, a clinical/diagnostic module can include computer code operable to, based at least in part on the EEG data, determine an indicator of ADHD, wherein the indicator supports a positive or negative ADHD evaluation.

A subgroup identification module, such as 116 and 134, can be adapted to correlate the indicator with the user's or clinician's evaluation data. In one embodiment, a subgroup identification module can include computer code operable to correlate the indicator with the user's or clinician's evaluation data. The subgroup identification module can be further adapted to determine, based at least in part on the correlation, at least one subgroup of the plurality of patients, wherein the correlation provides positive support for diagnosis of ADHD or provides support for further testing for complicating conditions before proceeding with diagnosis of ADHD in at least one patient within the at least one subgroup. In one embodiment, a subgroup identification module can include computer code operable to determine, based at least in part on the correlation, at least one subgroup of the plurality of patients, wherein the correlation provides positive support for diagnosis of ADHD or provides support for further testing for complicating conditions before proceeding with diagnosis of ADHD in at least one patient within the at least one subgroup.

An optional report module, such as 118 and 136, can be adapted to output an indication for at least one patient within the at least one subgroup, wherein the indication corresponds to whether the correlation provides positive support for diagnosis of ADHD or provides support for further testing for complicating conditions before proceeding with diagnosis of ADHD in the at least one patient. In one embodiment, a report module can include computer code operable to output an indication for at least one patient within the at least one subgroup, wherein the indication corresponds to whether the correlation provides positive support for diagnosis of ADHD or provides support for further testing for complicating conditions before proceeding with diagnosis of ADHD in the at least one patient.

Generally, each of the memories 110 and 128, and data storage devices or databases 124A-124N can store data and information for subsequent retrieval. In this manner, the system 100 can store various received or collected EEG and/or biological data or patient files in memory or a database associated with a client device, such as 104A, or a server, such as 106. The memories 110 and 128, and data storage devices or databases 124A-124N can be in communication with each other and/or other databases, such as a centralized database, or other types of data storage devices. When needed, data or information stored in a memory or database may be transmitted to a centralized database capable of receiving data, information, or data records from more than one database or other data storage devices. In other embodiments, the databases 124A-124N shown can be integrated or distributed into any number of databases or data storage devices.

Suitable processors for a client device 104A-104N and a server 106 may comprise a microprocessor, an ASIC, and state machine. Example processors can be those provided by Intel Corporation and Motorola Corporation. Such processors comprise, or may be in communication with media, for example computer-readable media, which stores instructions that, when executed by the processor, cause the processor to perform the elements described herein. Embodiments of computer-readable media include, but are not limited to, an electronic, optical, magnetic, or other storage or transmission device capable of providing a processor, such as the processors 108 and 126, with computer-readable instructions. Other examples of suitable media include, but are not limited to, a floppy disk, CD-ROM, DVD, magnetic disk, memory chip, ROM, RAM, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any computer-programming language, including, for example, C, C++, C#, Visual Basic, Java, Python, Perl, and JavaScript.

Client devices 104A-104N may also comprise a number of other external or internal devices such as a mouse, a CD-ROM, DVD, a keyboard, a display, or other input or output devices. As shown in FIG. 1, a client device such as 104A can be in communication with an output device via a communication or input/output interface, such as 122. Examples of client devices 104A-104N are personal computers, mobile computers, handheld portable computers, digital assistants, personal digital assistants, cellular phones, mobile phones, smart phones, pagers, digital tablets, desktop computers, laptop computers, Internet appliances, and other processor-based devices. In general, a client device, such as 104A, may be any type of processor-based platform that is connected to a network, such as 102, and that interacts with one or more application programs. Client devices 104A-104N may operate on any operating system capable of supporting a browser or browser-enabled application including, but not limited to, Microsoft Windows®, Apple OSX™, and Linux. The client devices 104A-104N shown include, for example, personal computers executing a browser application program such as Microsoft Corporation's Internet Explorer™, Netscape Communication Corporation's Netscape Navigator™, and Apple's Safari™, and Mozilla Firefox™

In one embodiment, suitable client devices can be standard desktop personal computers with Intel x86 processor architecture, operating a Microsoft® Windows® operating system, and programmed using a Java language.

A user, such as 120, can interact with a client device, such as 104A, via any number of input and output devices (not shown) such as an output display device, keyboard, and/or a mouse. In this manner, the user, such as 120, can access one or more webpages located on a website server host, such as 106, via an Internet browser application program operating on a client device, such as 104A. In the embodiment shown, a user 120 can receive information associated with at least one ADHD patient via the client device 104A. In one example, the client device 104A can access or otherwise receive EEG or biological data associated with one or more patients. In another example, the client device 104A can access or otherwise receive user's or clinician's evaluations for patients identified with ADHD as a primary diagnosis. In yet another example, the client device 104A can receive one or more patient inputs to an online questionnaire or series of questions designed to elicit patient information associated with diagnosing ADHD in the patient. In any instance, the client device 104A can provide one or more options for the user 120 to request or otherwise retrieve certain information accessible by the client device 104A.

After the client device 104A receives a user input, the client device 104A can, in certain instances, identify a plurality of patients having ADHD as a primary diagnosis. For example, the client device 104A can obtain previously stored EEG or biological data for each of the plurality of patients, wherein the EEG or biological data can be analyzed and/or evaluated to support a positive or negative ADHD evaluation. In another example, the client device 104A can collect some or all previously submitted clinical evaluations associated with a plurality of patients having ADHD as a primary diagnosis. In yet another example, the client device 104A can analyze and determine from one or more patient's and/or other suitable informants' responses to an online questionnaire or series of questions, a plurality of patients having ADHD as a primary diagnosis. In any instance, based at least in part on the EEG or biological data, the client device 104A can determine an indicator of ADHD, wherein the indicator supports a positive or negative ADHD evaluation.

The client device 104A can correlate the indicator with a user's or clinician's evaluation data, and based at least in part on the correlation, the client device 104A can determine at least one subgroup of the plurality of ADHD patients, wherein the correlation provides positive support for diagnosis of ADHD or provides support for further testing for complicating conditions before proceeding with diagnosis of ADHD in at least one patient within the at least one subgroup. The client device 104A can provide an output to the user 120, wherein the user 120 can view a report or other indication corresponding to whether the correlation provides positive support for diagnosis of ADHD or provides support for further testing for complicating conditions before proceeding with diagnosis of ADHD in at least one patient within the at least one subgroup.

Other system embodiments in accordance with the invention can include fewer or greater numbers of components and may incorporate some or all of the functionality described with respect to the system components shown in FIG. 1. One will appreciate that components of the system 100 shown in and described with respect to FIG. 1 are provided by way of example only. Numerous other operating environments, system architectures, and device configurations are possible. Accordingly, embodiments of the invention should not be construed as being limited to any particular operating environment, system architecture, or device configuration.

In one example, a data collection module similar to 112 and 130, clinical/diagnostic module similar to 114 and 132, subgroup identification module similar to 116 and 134, and report module similar to 118 and 136, according to an embodiment of the invention, can be implemented by the NEBA™ system, provided by Lexicor Medical Technology, Inc. In this embodiment, the system 100 can support a 15-20 minute non-invasive office-based test developed to provide a relatively reliable, quantitative measurement of neural activity in the cortex at the electrode CZ (of the International 10/20 electrode placement system). The functionality of some or all of the modules 112-118, 130-136 shown in FIG. 1 can be performed by the NEBA™ system using some or all of the following high-level sub-system components: (1) CEEG (compact EEG) recording system, (2) EEG data archive and communications system (EDACS), and (3) NEBA™ analysis system. The high-level sub-system components can be used to compare an individual patient's quantified EEG with certain clinical reference values. The system 100 can provide a clinician or user with a specific EEG marker of activity, for example, in the form of a power ratio. In this example, a power ratio can be computed by dividing the average percent power in the theta frequency band (about 4-7.5 Hz) by the average percent power in the beta frequency band (about 13-20.5 Hz) and is termed the theta/beta ratio (TBR). TBR cutoffs provided are specific to the NEBA™ system processing and analysis of EEG, but can be adjusted as needed or desired in other system embodiments. TBR cutoffs specify categories of "positive," "negative," or "uncertain" for certain predefined or specified ranges or thresholds of TBR associated with ADHD.

In one embodiment, TBR cutoffs can be determined for one or more ranges or thresholds and corresponding categories, for example, as follows: in at least one patient within a predefined or specified age range with ADHD identified as a primary diagnosis by a clinician or user, EEG data comprising a theta/beta ratio (TBR) calculation within a predefined or specified range provides positive support for diagnosis of ADHD, EEG data comprising a theta/beta ratio (TBR) calculation within a predefined or specified range provides a suggestion for further testing for complicating conditions before proceeding with diagnosis of ADHD, and EEG data comprising a theta/beta ratio (TBR) calculation within a predefined or specified range provides a strong recommendation for further testing for complicating conditions before proceeding with diagnosis of ADHD; in at least one patient with whom ADHD presence as a primary diagnosis is considered to be "uncertain" by a clinician or user, EEG data comprising a theta/beta ratio (TBR) calculation within a predefined or specified range provides a suggestion for further testing with focus on ruling in/out ADHD before considering other disorders for primary diagnosis, EEG data comprising a theta/beta ratio (TBR) calculation within a predefined or specified range provides a suggestion for further testing for complicating conditions before proceeding with diagnosis of ADHD, and EEG data comprising a theta/beta ratio (TBR) calculation within a predefined or specified range provides a strong recommendation for further testing for complicating conditions before proceeding with diagnosis of ADHD; and in at least one patient with whom ADHD is determined to be absent or secondary to another condition by a clinician or user, EEG data comprising a theta/beta ratio (TBR) calculation within predefined or specified ranges provides a suggestion for reviewing other possibilities for an elevated theta/beta ratio (TBR), and EEG data comprising a theta/beta ratio (TBR) calculation within a predefined or specified range provides confirmatory support for absence of ADHD.

In one embodiment, TBR cutoffs can include one or more of the following ranges or thresholds and corresponding categories, for example, as follows: in at least one patient aged around 6.00 to 11.99 years old with ADHD identified as a primary diagnosis by a clinician or user, EEG data comprising a theta/beta ratio (TBR) calculation within a predefined or specified range provides positive support for diagnosis of ADHD, EEG data comprising a theta/beta ratio (TBR) calculation within a predefined or specified range provides a suggestion for further testing for complicating conditions before proceeding with diagnosis of ADHD, and EEG data comprising a theta/beta ratio (TBR) calculation within a predefined or specified range provides a strong recommendation for further testing for complicating conditions before proceeding with diagnosis of ADHD.

In another embodiment, TBR cutoffs can include one or more of the following ranges or thresholds and corresponding categories, for example, as follows: in at least one patient aged around 12.00 to 17.99 years old with ADHD identified as a primary diagnosis by a clinician or user, EEG data comprising a theta/beta ratio (TBR) calculation within a predefined or specified range provides positive support for diagnosis of ADHD, EEG data comprising a theta/beta ratio (TBR) calculation within a predefined or specified range provides a suggestion for further testing for complicating conditions before proceeding with diagnosis of ADHD, and EEG data comprising a theta/beta ratio (TBR) calculation within a predefined or specified range provides a strong recommendation for further testing for complicating conditions before proceeding with diagnosis of ADHD.

In one embodiment, TBR cutoffs can be determined for one or more ranges or thresholds and corresponding categories, for example, as follows: in at least one patient aged less than 6.00 years old with ADHD identified as a primary diagnosis by a clinician or user, EEG data comprising a theta/beta ratio (TBR) calculation within a predefined or specified range provides positive support for diagnosis of ADHD, EEG data comprising a theta/beta ratio (TBR) calculation within a predefined or specified range provides a suggestion for further testing for complicating conditions before proceeding with diagnosis of ADHD, and EEG data comprising a theta/beta ratio (TBR) calculation within a predefined or specified range provides a strong recommendation for further testing for complicating conditions before proceeding with diagnosis of ADHD.

In one embodiment, TBR cutoffs can be determined for one or more ranges or thresholds and corresponding categories, for example, as follows: in at least one patient aged greater than 17.99 years old with ADHD identified as a primary diagnosis by a clinician or user, EEG data comprising a theta/beta ratio (TBR) calculation within a predefined or specified range provides positive support for diagnosis of ADHD, EEG data comprising a theta/beta ratio (TBR) calculation within a predefined or specified range provides a suggestion for further testing for complicating conditions before proceeding with diagnosis of ADHD, and EEG data comprising a theta/beta ratio (TBR) calculation within a predefined or specified range provides a strong recommendation for further testing for complicating conditions before proceeding with diagnosis of ADHD.

In other example embodiments, other TBR cutoffs can be determined for one or more predefined or specified ranges or thresholds and corresponding categories of patients.

In one embodiment, a data collection module similar to 112 and 130, can collect biological data such as EEG data using noninvasive electrodes that are placed on a patient's head. For example, an operator can place a single recording electrode (CZ) on the patient's scalp with conductive gel to ensure a suitable connection for data collection. The electrode is placed in accordance with the International 10-20 system using an electrode headband with a ground electrode near FZ and linked ears reference. Electro-oculography (EOG) can be used to monitor eye blinks and gross eye movement. In certain instances, one or more trained technicians or users can perform manual (visual detection) and algorithm-based (50 µV threshold) artifacting of the EEG data using frequency spectrum analysis software. In any instance, EEG data can be processed with frequency spectrum analysis software and/or other techniques or routines to transform the EEG data into the frequency domain and perform calculations to determine the TBR. The EEG data and/or TBR for the patient of interest can be used to support an ADHD evaluation of the patient.

In one instance, an output from a data collection module, such as 112 and 130, can be provided for a user or clinician, such as 120. Output from the data collection module, such as 112 and 130, can include, for example, EEG results, cutoffs, and a clinical database comparison that can be presented in a report, such as shown in FIG. 2.

In one example, a data collection module, such as 112 and 130, can present an indicator of ADHD, such as a patient's theta/beta ratio (TBR), to a clinician or user 120 as follows:

"The result is (positive/negative/uncertain) for a significant increase in TBR, as processed by standardized NEBA™ methods and compared to the NEBA™ clinical database. Please refer to manual for further information supporting interpretation of TBR."

Figure 2:
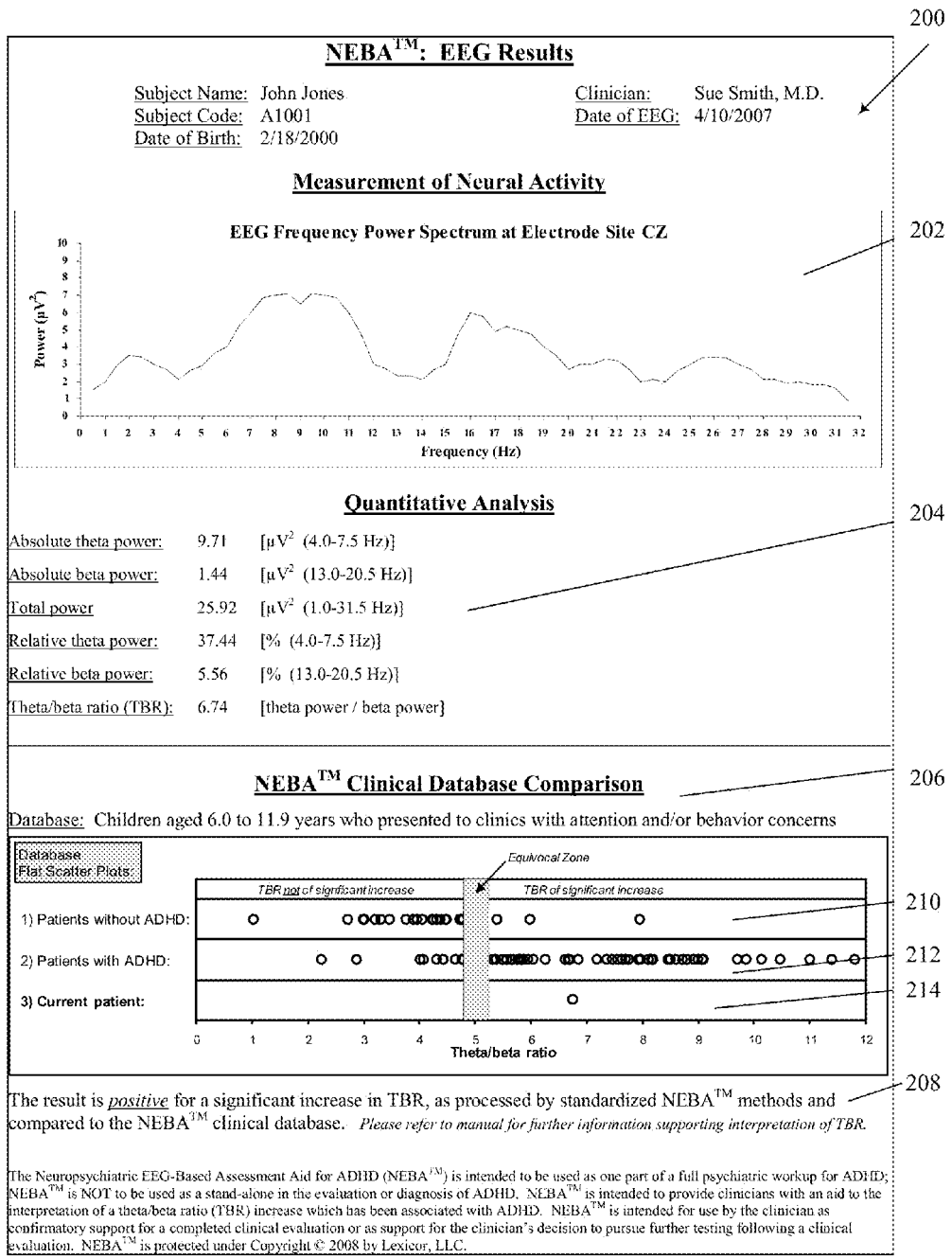
FIG. 2 illustrates an example summary for a particular patient's EEG results in accordance with an embodiment of the invention.

As shown in FIG. 2, in accordance with an embodiment of the invention, an example output 200 from a data collection module, such as 112 or 130, can provide a summary for a particular patient's EEG or other biological data results, including a measurement of neural activity 202, a quantitative analysis of EEG data 204, a clinical database comparison 206, and an EEG data interpretation supporting an ADHD evaluation 208.

In this embodiment, a data collection module, such as 112 or 128, can use the collected EEG data and/or TBR to support an ADHD evaluation of the patient. For example, after the data collection module collects or receives EEG or biological data for a patient of interest, the data collection module can determine a TBR for the patient. The data collection module can then compare the patient's TBR with a population sample having one or more similar characteristics to the patient's demographics, such as age. Based at least in part on the comparison, the data collection module can support an ADHD evaluation of the patient, such as positive or a negative evaluation, by providing confirmatory support for a user's or clinician's ADHD evaluation or providing a recommendation of further testing for complicating conditions that could be of concern to the user's or clinician's ADHD evaluation. As shown in FIG. 2, the collected EEG or biological data in 202 can be monitored and stored by the data collection module. A quantitative analysis 204 by the data collection module can determine certain variables for the collected EEG or biological data, for instance, absolute theta power, absolute beta power, total power, relative theta power, relative beta power, and theta/beta ratio (TBR). As shown in 206, using some or all of the variables from the quantitative analysis 204, the data collection module can compare the patient's TBR with a population sample of one or more patients or other subjects having one or more similar characteristics to the patient's demographics. In this example, children aged 6.0 to 11.9 years old who presented attention and/or behavior problems were selected as a population sample. The example in FIG. 2 shows a pair of flat scatter plots 210 and 212, which respectively illustrate the TBRs of patients without ADHD and the TBRs of patients with ADHD. A third plot 214 below the pair of scatter plots 210, 212 illustrates the TBR of the patient of interest. As shown in FIG. 2, the third plot 214 indicates a patient of interest's TBR to be about 6.74, which compared to the pair of scatter plots 210, 212 is above the equivocal zones and within the ranges of TBR of significant increase relative to the population sample. As indicated by 208, an output of "The result is positive for a significant increase in TBR, as processed by standardized NEBA™ methods and compared to the NEBA™ clinical database. Please refer to manual for further information supporting interpretation of TBR." In any instance, based at least in part on the comparison of the patient of interest's TBR with those of the selected population of sample, an ADHD evaluation of the patient, such as positive or a negative evaluation, can be supported by the data collection module, by providing confirmatory support for a user's or clinician's ADHD evaluation or providing a recommendation of further testing for complicating conditions that could be of concern to the user's or clinician's ADHD evaluation.

In one embodiment, to interpret a patient's case, a user such as 120 or clinician first performs or otherwise receives a clinical evaluation for the patient of interest and determines whether ADHD is present as the primary diagnosis. A primary diagnosis may be defined as meaning that ADHD would be the condition managed and treated first by a user 120 or clinician, and that other conditions may have been ruled out as a primary diagnosis. The user 120 or clinician can then input the clinical evaluation to the system 100, or alternatively, can refer to results from the system 100. In certain instances, a set of guidelines, such as the NEBA™ Interpretation Guidelines shown in FIG. 4, can offer a user 120 or clinician, for example, two general possibilities that depend on the agreement of system 100 with the evaluation: (1) Confirmatory support; or (2) Further clinical testing recommended.

In another embodiment, automated interpretation of a patient's case could be performed by the client device, such as 104A. For example, using an online questionnaire or series of questions designed to elicit patient information associated with diagnosing ADHD in the patient, the data collection module can receive responses from the patient and/or other suitable informant(s) to the questionnaire or series of questions. The questions can include, but are not limited to, "Are you generally restless or fidgety?", "Do you have difficulty following instructions?", and "Are you easily distracted?", as well as "Is the child or adolescent generally restless or fidgety?", "Does the child or adolescent have difficulty following instructions?", and "Is the child or adolescent easily distracted?". Based at least in part on the responses from the patient and/or suitable informant(s), the data collection module can provide an evaluation for the patient of interest and determine whether ADHD is present as the primary diagnosis. The automated evaluation can then be utilized in lieu of a user's or clinician's evaluation.

FIG. 3 illustrates general example interpretations delineated by a correlation of a clinical ADHD evaluation with a system result in accordance with an embodiment of the invention. As shown in FIG. 3, a three by three grid 300 can be used to correlate an ADHD evaluation (negative, uncertain, positive) with the system result (negative, uncertain, positive). The grid 300 and associated interpretations shown in FIG. 3 can be stored in a memory, such as 110 and 128, and/or one or more data storage devices or databases, such as 124A-124N, wherein a subgroup identification module or application program, such as 116 and 134, can access the grid 300 and correlate an evaluation of ADHD with an ADHD indicator. Other grids, data structures, and combinations of evaluations and system results can be used to correlate an evaluation of ADHD with an ADHD indicator. In use, the grid 300 and associated interpretations correlate the result of the ADHD evaluation with the ADHD indicator or system result to obtain an interpretation. For example, a user or clinician's positive ADHD evaluation correlated with a positive system result equates to a "Confirmatory Support" interpretation in the upper right corner of the grid 300. By way of further example, a positive user or clinician's ADHD evaluation correlated with a negative system result equates to a "Strongly Recommend Further Clinical Testing" interpretation in the upper left corner of the grid 300. Equivocal (uncertain) zones are highlighted in grey in the grid 300.

As shown by the embodiment of FIG. 3, the absence of ADHD in a particular patient can be determined by the user or clinician after a clinical ADHD evaluation; that is, if ADHD DSM-IV criteria are not present, there can be no clinical diagnosis of ADHD. In certain embodiments, the absence of ADHD in a particular patient can be supported by a data collection module or application program, such as 112 and 130, operating with a clinical/diagnostic module or application program, such as 114 and 132. For example, data collection module or application program, such as 112, and a clinical/diagnostic module or application program, such as 114, can include computer code to receive input from a user or clinician, such as 120, indicating a result of a clinical ADHD evaluation. In another example, a data collection module or application program, such as 112 and 130, operating in conjunction with a clinical/diagnostic module, such as 114 and 132, can include computer code to evaluate responses from a patient and/or other suitable informant to an online questionnaire or series of questions, and based at least in part on the responses from the patient and/or suitable informant, can provide an ADHD evaluation, which identifies one or more patients having ADHD as a primary diagnosis. In either instance, a subgroup identification module or application program, such as 116 and 134, can correlate the ADHD evaluation with the system result to obtain an interpretation.

The example equivocal zone in FIG. 3 can offer a graded strength behind certain recommendations. For instance, if a system result is equivocal (uncertain), the example guidelines can "suggest" further clinical testing. If there is disagreement between the user or clinician's evaluation and a system negative result, the example guidelines can "strongly recommend" further clinical testing. When further clinical testing is recommended, suggestions can be provided for the initial focus as shown in FIG. 4.

Example details of the NEBA™ Interpretation Guidelines are shown in FIG. 4 in accordance with an embodiment of the invention. In continuing the above example, for a user or clinician's positive ADHD evaluation correlated with a positive system result in the grid 400 of FIG. 4, the full interpretation equates to a "Confirmatory support for presence of ADHD. Suggest using EEG as part of discussion with patient on biological aspects of disorders." evaluation shown in the first horizontal line of the grid 400. Continuing the other example above, for a positive user or clinician's ADHD evaluation correlated with a negative system result, the full interpretation equates to a "Strongly recommend further clinical testing with focus on ruling in/out other conditions before proceeding with ADHD as primary diagnosis." evaluation shown in the third horizontal line of the grid 400. Similar to grid 300, grid 400 and associated interpretations shown in FIG. 4 can be stored in a memory, such as 110 and 128, and/or one or more data storage devices or databases, such as 124A-124N, wherein a subgroup identification module or application program, such as 116 and 134, can access the grid 400 and correlate an evaluation of ADHD with an ADHD indicator. Other grids, data structures, and combinations of evaluations and system results can be used to correlate an evaluation of ADHD with an ADHD indicator.

In this embodiment, functionality provided by the system, such as the NEBA™ system or system 100 in FIG. 1, can be one part of a psychiatric workup for ADHD. In certain embodiments, the functionality provided by the system can be used to support the evaluation or diagnosis of ADHD, and in other embodiments, the functionality of the system is not to be exclusively used in the evaluation or diagnosis of ADHD. In any instance, the functionality provided by the system can aid in the interpretation of a patient's TBR increase in the context of certain cutoffs, processing, standardization, and database comparison provided by the system. For example, the system can be used by a user or clinician as confirmatory support for a completed clinical evaluation or as support for the user or clinician's decision to pursue further testing following a clinical evaluation.

In one embodiment, a system, such as the NEBA™ system or system 100 in FIG. 1, can separate an ADHD group of patients into two subgroups: (1) a subgroup receiving confirmatory support for a completed clinical evaluation, and (2) a subgroup receiving support for the user or clinician's decision to pursue further testing following a clinical evaluation. An example separation of an ADHD group into subgroups by a process implemented by a system such as 100 is illustrated in FIG. 5, which represents one example how a clinician or user such as 120 could integrate the system 100 or system similar to the NEBA™ system into a patient evaluation process.

Figure 5:
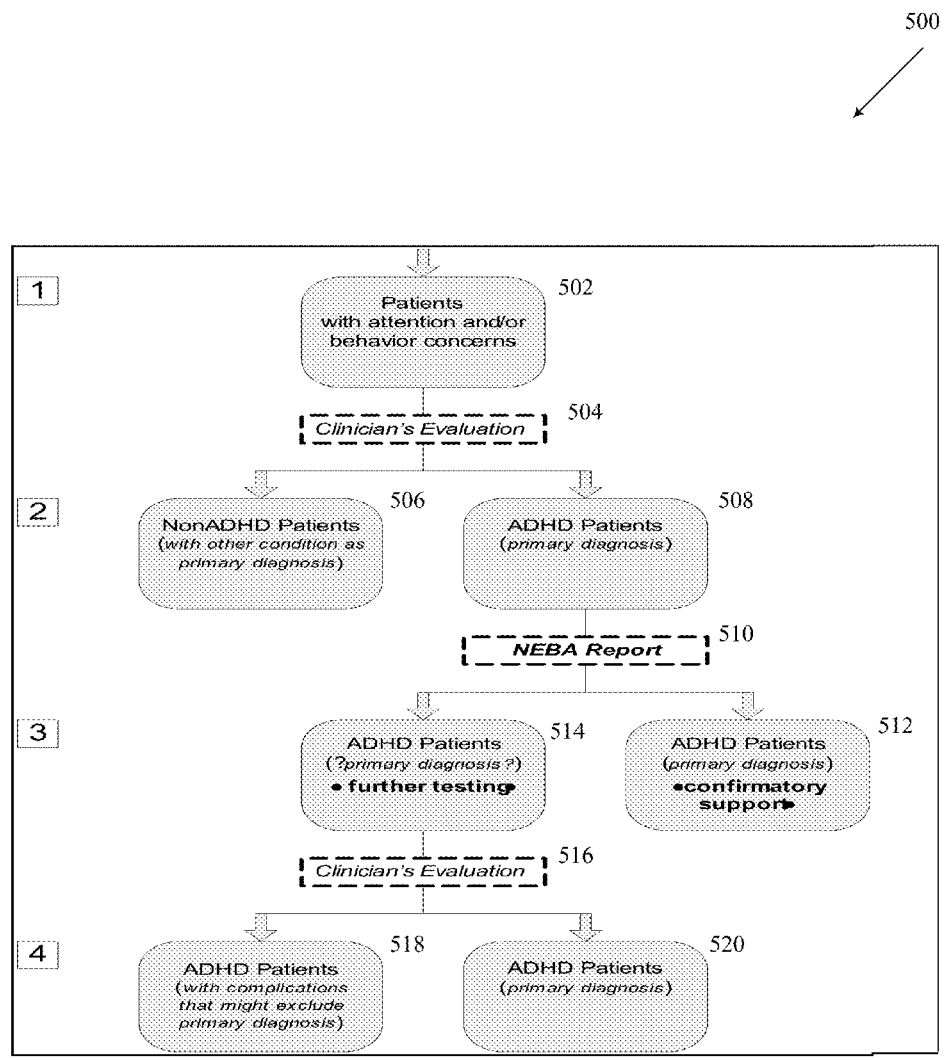
FIG. 5 illustrates an example method in accordance with an embodiment of the invention.

In FIG. 5, the method 500 begins at block 502, in which data for patients with attention and/or behavior concerns, such as ADHD, is received. For example, in some instances, data associated with one or more patients with attention and/or behavior concerns can be input to the system, such as 100 in FIG. 1, by a clinician or user, such as 120. In another example, data associated with one or more patients with attention and/or behavior concerns can be retrieved by a data collection module, such as 112 in FIG. 1, from a data storage device, such as 124A. In either instance, a data collection module or application program, such as 112 or 130, can receive the data associated with one or more patients.

Block 502 is followed by block 504, in which a diagnostic evaluation for each patient is received. For example, in some instances, a clinician or user, such as 120, can perform a diagnostic or clinical ADHD evaluation per the standard of his or her practice, and the clinical evaluation can be submitted to a data collection module, such as 112 in FIG. 1. In other instances, an evaluation can be supported using a clinical evaluation from a clinical/diagnostic module or application program, such as 114 in FIG. 1.

In any instance, based at least in part on the patients' clinical evaluations, the patients can initially be divided into at least two groups as shown in blocks 506 and 508. For example, based at least in part on the user's or clinician's evaluation, the patients can be separated into two groups: (1) Patients with ADHD (full threshold) as primary diagnosis in block 508, and (2) All other patients (ADHD is absent or secondary or sub-threshold) in block 506. At this point, the clinician or user such as 120 may decide to apply certain functionality of the system, such as the NEBA™ system, to the patients who have ADHD as primary diagnosis, such as those determined in block 508.

Block 508 is followed by block 510, in which EEG or biological data from each of the patients who have ADHD as primary diagnosis is used to support a positive or negative ADHD evaluation. For example, as explained above with respect to FIG. 2, using a comparison of a patient's TBR (theta-beta ratio) with a predefined population sample, a clinical/diagnostic module or application program, such as 114 and 132, and subgroup identification module or application program, such as 116 and 134, can facilitate support of an ADHD evaluation. In this embodiment, based at least in part on the EEG data, the ADHD patients (primary diagnosis) can be separated into two groups as shown in blocks 512 and 514: (1) ADHD patients receiving confirmatory support in block 512, and (2) ADHD patients receiving a recommendation for further testing in block 514.

Block 514 is followed by block 516, in which an additional diagnostic evaluation for each patient receiving a recommendation for further testing is received, and based on the results of such testing a determination for each patient is further made. For example, in some instances, a clinician or user such as 120 can decide whether to follow a recommendation for further testing from block 514. The further testing would be performed by the clinician or user such as 120 per the standard of his or her practice, or performed by a specialist through referral. The further testing could determine whether any complicating conditions are present which may be of concern to an ADHD evaluation and might lead to exclusion of ADHD from primary diagnosis for the patient of interest.

In another embodiment, a subgroup identification module, such as 116 and 134, can receive additional diagnostic information from a database, such as 124A-124N or a user or clinician, such as 120. Based at least in part on the additional diagnostic information received, the subgroup identification module, such as 116 and 134, can support separation of the group of ADHD patients recommended for further testing into two further subgroups.

In any instance, block 518 represents the subgroup of patients in which further testing is performed confirming the patient with ADHD as previously diagnosed by clinician or user has complicating conditions that may be of concern to an ADHD evaluation and might exclude ADHD from a primary diagnosis, and block 520 represents the subgroup of patients in which further testing is performed confirming the ADHD evaluation as the primary diagnosis and confirming that complicating condition are absent or present but do not lead to excluding ADHD from a primary diagnosis.

Returning to the results of the additional testing, such testing can indicate the presence of possible complications or complicating conditions. Possible complications or complicating conditions include, but are not limited, to the following: (1) a psychiatric disorder that could lead to ADHD exclusion, such as (a) pervasive developmental disorders, psychotic disorders, bipolar disorders, and disorders caused by a stressing event, namely post-traumatic stress disorder and adjustment disorder; (2) a medical or neurological condition that could simulate ADHD, such as conditions involving head injury with ongoing problems, sensory integration dysfunction, auditory processing disorder, substance abuse, tobacco exposure, anemia, headaches affecting attention, congenital encephalopathy, cerebral palsy, mild mental retardation, neuromaturational delays/soft signs, and influence of asthma medications; (3) an uncorrected vision or hearing problem which could simulate ADHD; (4) history of adverse events and/or no improvement with ADHD medications, such as cardiac problems, tics, insomnia, weight loss, depression, compulsiveness, irritability, anxiety, withdrawal, lethargy, nausea, and headaches; (5) aggression and/or anger issues as a primary concern such as anger/aggression as primary concern and/or arising specifically with ADHD treatment, probable to definite conduct disorder (CD), and oppositional defiant disorder (ODD); (6) doing well academically and intellectually, such as reported in interview and/or questionnaire as doing well academically/intellectually, no special education, and no repeated grade; (7) dissatisfaction with a previous or current ADHD diagnosis, such as when a patient may have presented because further evaluation was wanted after previous ADHD diagnosis, or because evaluation was sought for other disorders not ADHD, or patient may have had general dissatisfaction with ADHD treatment, or parents and/or teachers may have both ruled out ADHD (all scale scores <80th percentile). A clinical/diagnostic module, such as 114 and 132, can receive this additional information for some or all of the ADHD patients from block 514, and based at least in part on this additional information can separate the ADHD patients into at least two subgroups.

Thus, in block 516, information from an additional diagnostic evaluation can be used to separate the ADHD patients from block 514 into two subgroups in blocks 518 and 520.

After blocks 518 and 520, the method 500 ends.

The method 500 can be implemented with the system 100 shown in FIG. 1. Other embodiments of the method 500 can include fewer or greater numbers of elements, and may be implemented with other system embodiments in accordance with the invention.

FIGS. 6-20 illustrate various supporting data for an example system and process implementation for at least one embodiment of the invention. In this embodiment, one system measure or indicator (EEG theta/beta ratio) can be reliably determined, and the intraclass correlation coefficient (ICC) of repeated system measures or indicators (test-retest reliability) was evaluated at about 0.83. In further evaluations, ICC was about 0.85 and about 0.88. To determine reliability, system EEG measurements were recorded on two separate visits from children and adolescents (n=198) aged 6.00 to 17.99 years who presented to 13 clinics with attention and behavior concerns. Three different EEG technicians separately performed artifact removal on system EEG data resulting in the three ICC results.

In support of system diagnostic accuracy per the intended use, positive predictive value (PPV) was about 94%, negative predictive value (NPV) was about 80%, sensitivity was about 82%, specificity was about 93%, and overall accuracy was about 87%. To evaluate diagnostic accuracy per the intended use, FIG. 6 represents the true and false answers of the system. A true answer for a system result of confirmatory support "CS" is when a system positive for theta/beta ratio (TBR) being relatively high (EEG-yes) agrees with the clinician's positive diagnosis (ADHD-yes). A false answer for confirmatory support "CS" is when a system positive (EEG-yes) disagrees with the clinician's negative diagnosis (ADHD-no). Positive predictive value (PPV) represents the chance that when an individual patient receives a system positive, that the patient has ADHD as primary diagnosis. To evaluate the performance of the system result of recommendation for further testing "FT", it was also necessary to determine whether clinically meaningful conditions were likely to be found. Conditions can be considered clinically meaningful to the user or clinician's diagnosis if the conditions may be of concern to an ADHD evaluation and might lead the clinician to exclude ADHD from primary diagnosis. Conditions or complications that were considered in the evaluation of system were those listed above. When evaluating per the intended use, a system negative (EEG-no; TBR is relatively low) for an ADHD patient results in a recommendation for further testing for other conditions (complications) that may be of concern to an ADHD evaluation and might lead a user or clinician to exclude ADHD as primary diagnosis. Negative predictive value (NPV) represents the chance that when an individual patient receives a system negative (EEG-no), that the patient does not have ADHD as primary diagnosis (ADHD-no). When analyzing per the intended use, NPV includes reference to the presence or absence of complications that may be of concern to an ADHD evaluation and might lead to exclusion of ADHD from primary diagnosis.

FIGS. 7-10 illustrate relative diagnostic accuracies and comparisons for various sample populations evaluated using a system, such as 100 in FIG. 1, in accordance with an embodiment of the invention. Results for system diagnostic accuracy per the intended use are listed in FIG. 7. Overall diagnostic accuracy for the adolescents and children tested is about 87%. As shown in FIG. 7, groups of adolescents and children were tested, and statistics for sensitivity, specificity, positive predictive value, and negative predictive value were obtained.

FIG. 8 illustrates example results that show that the performance of a system, such as 100 in FIG. 1, is consistent across demographic groups in accordance with an embodiment of the invention. As shown in FIG. 8, demographic groups such as ages 6-11 years vs. 12-17 years, female vs. male, white vs. non-white, and upper/middle class vs. working/lower class were compared, and statistics for overall accuracy were obtained.

FIG. 9 illustrates example results that show that the presence of other common childhood disorders do not interfere with the performance of the system, such as 100 in FIG. 1, in accordance with an embodiment of the invention. As shown in FIG. 9, the presence of different general types of disorders such as anxiety disorder, mood disorder, disruptive disorder, and learning disorder were compared, and statistics for overall accuracy were obtained.

FIG. 10 illustrates example results that show that the performance of a system, such as 100 in FIG. 1, is consistent in different clinics run by users or clinicians from different fields who are serving different patient populations from a variety of communities and regions in accordance with an embodiment of the invention. As shown in FIG. 10, different user or clinician types such as psychiatry, pediatrics, and psychology; different sectors such as private vs. academic; different regions such as South, West, Northeast, Midwest were compared, and statistics for overall accuracy were obtained.

In the intended use, certain embodiments such as the system 100 in FIG. 1 can essentially separate an ADHD group into two subgroups: (1) ADHD-yes/EEG-yes (receiving confirmatory support, "CS"), and (2) ADHD-yes/EEG-no (receiving a recommendation for further testing, "FT"). For the certain embodiments such as the system to be of clinical value, the CS (ADHD patients with "EEG-yes") and FT (ADHD patients with "EEG-no") subgroups should have statistically significant differences in clinical characteristics that are meaningful to the clinician's evaluation of ADHD. Thus, differences in clinical characteristics of ADHD patients with "EEG-no" should support that the result of further testing for this subgroup would be of benefit to the clinical evaluation.

In testing of certain system embodiments of the invention, for example, the system shown as 100 in FIG. 1, various odds ratio (OR) plots in FIGS. 11-20 show that the system can separate ADHD patients into two subgroups with clinically meaningful differences. All of the OR results are statistically significant (statistical significance was supported when the 95% confidence interval did not cross 1 on the plot.) The differences are clinically meaningful because the evaluated conditions would be of concern to an ADHD evaluation and/or could lead a user or clinician to exclude ADHD from primary diagnosis. Therefore these results substantiate that a system result of further testing, in accordance with an embodiment of the invention, would be of benefit to the clinical evaluation.

FIGS. 11-20 illustrate various statistical clinical support in the form of odds ratio plots for an example implementation of an embodiment of the invention.

Figure 11:
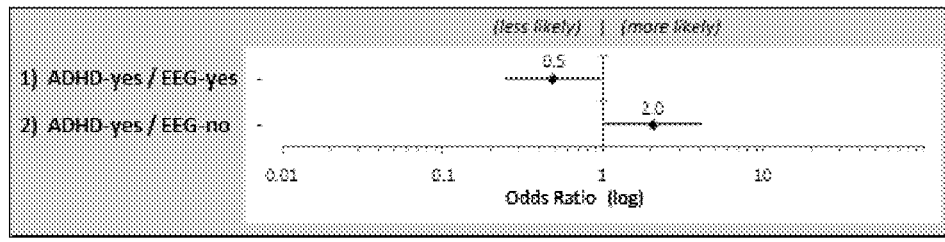
FIGS. 11-20 illustrate various statistical clinical support in the form of odds ratio plots for an example implementation of an embodiment of the invention.

FIG. 11 shows that the ADHD-yes/EEG-no subgroup (NEBA™: further testing) was about twice as likely (by odds) to have a psychiatric disorder that could lead to ADHD exclusion from primary diagnosis in accordance with an embodiment of the invention. Note that in FIG. 11, psychiatric disorders include, but are not limited to, pervasive developmental disorders, psychotic disorders, and bipolar disorders. Disorders also include those caused by a stressing event, namely post-traumatic stress disorder and adjustment disorder.

Figure 12:
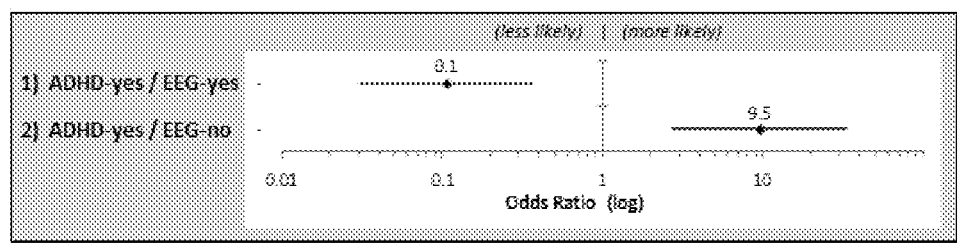

FIG. 12 shows that the ADHD-yes/EEG-no subgroup (NEBA™: further testing) was approximately over 9 times more likely to have a medical or neurological condition that could simulate ADHD in accordance with an embodiment of the invention. Note that in FIG. 12, medical/neurological conditions that may simulate ADHD include, but are not limited to, head injury with ongoing problems, sensory integration dysfunction, auditory processing disorder, substance abuse, tobacco exposure, anemia, headaches affecting attention, congenital encephalopathy, cerebral palsy, mild mental retardation, neuromaturational delays/soft signs, influence of asthma medications).

Figure 13:
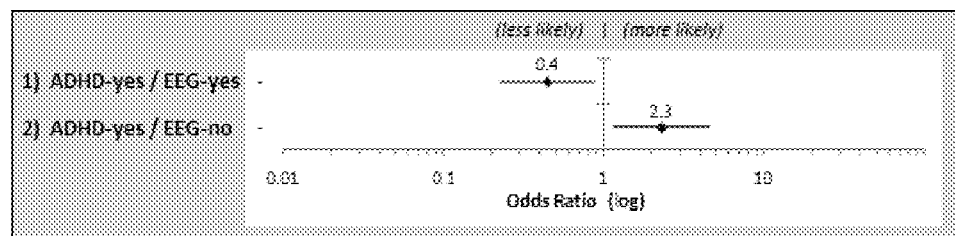

FIG. 13 shows that the ADHD-yes/EEG-no subgroup (NEBA™: further testing) was approximately over twice as likely to have uncorrected vision or hearing problems that could also simulate ADHD in accordance with an embodiment of the invention.

Figure 14:
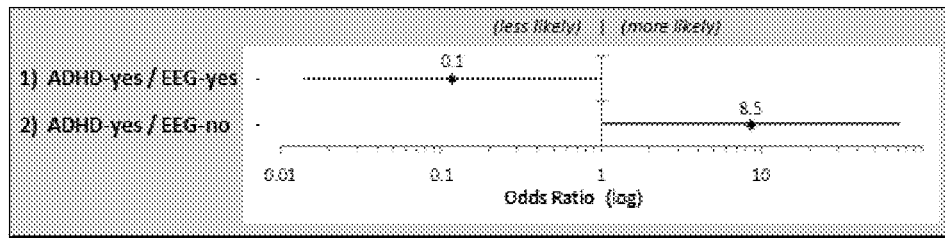
Figure 15:
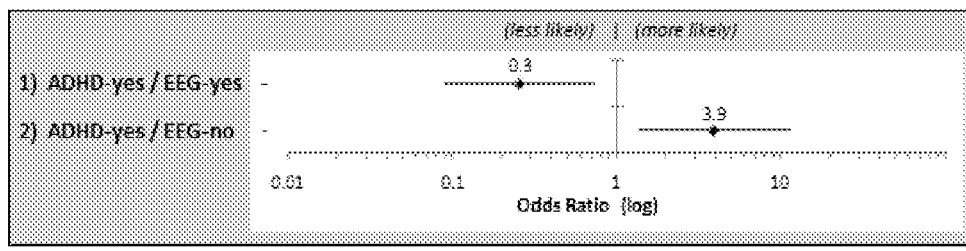

FIGS. 14 and 15 show that the ADHD-yes/EEG-no subgroup (NEBA™: further testing) was more likely to have had a history of problems with ADHD medications; i.e. approximately over 8 times more likely to have experienced no improvement with ADHD medications, and almost 4 times more likely to have experienced adverse events in accordance with an embodiment of the invention. Adverse events with medications were of significant concern and include cardiac problems, tics, depression, anxiety, compulsiveness, insomnia, weight loss, and headaches. Note that adverse events can include, but not limited to, cardiac problems, tics, insomnia, weight loss, depression, compulsiveness, irritability, anxiety, anger, withdrawal, lethargy, nausea, and headaches.

Figure 16:
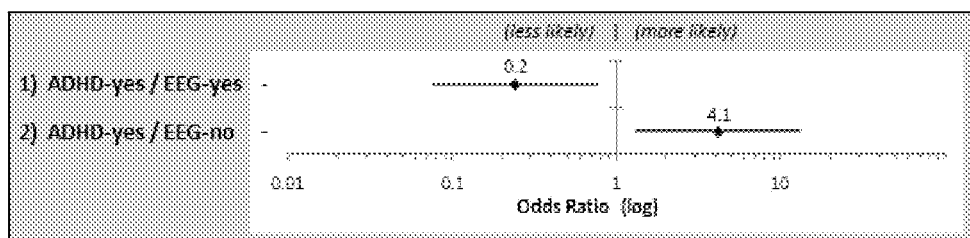
Figure 17:
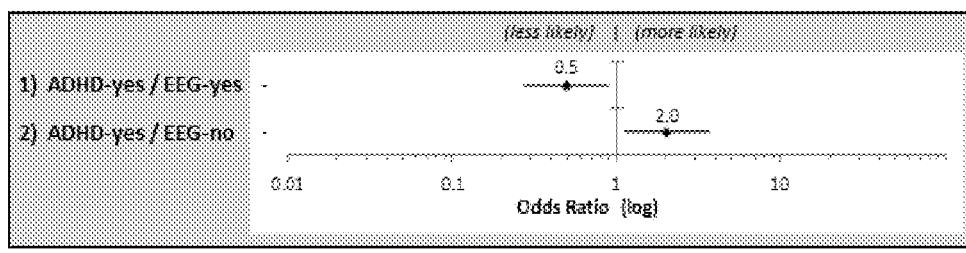

FIGS. 16 and 17 show that the ADHD-yes/EEG-no subgroup (NEBA™: further testing) was approximately over 4 times more likely to have presented with anger as a primary concern and twice as likely to have aggression as a primary concern in accordance with an embodiment of the invention. Note in FIG. 16 these patients presented with anger as a primary concern and/or had experienced anger arising with use of ADHD medications. Note in FIG. 17 these patients presented with aggression as a primary concern and/or had experienced aggression arising with use of ADHD medications. Many were diagnosed with probable to definite conduct disorder (CD) and/or oppositional defiant disorder (ODD).

Figure 18:
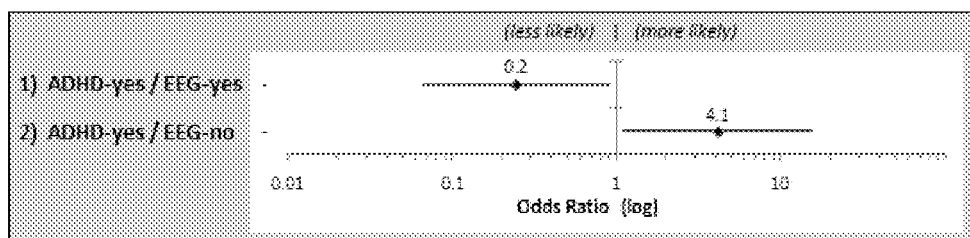
Figure 19:
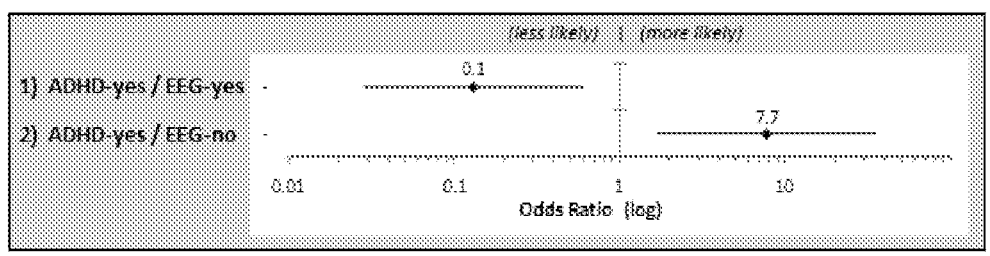
Figure 20:
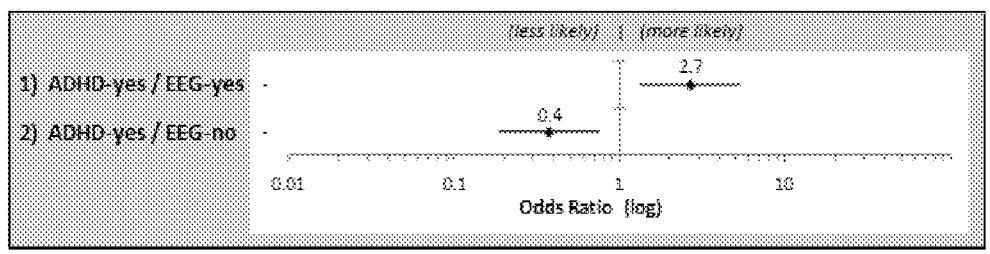

FIGS. 18 and 19 show that the ADHD-yes/EEG-no subgroup (NEBA™: further testing) was approximately over 4 times more likely to be doing well academically and intellectually, and approximately over 7 times more likely to express dissatisfaction with a previous or current diagnosis of ADHD in accordance with an embodiment of the invention. These outcomes were consistent with the initial "gut" response of the user or clinician to the patient, in that this subgroup was about 60% less likely to have given the user or clinician an initial impression of ADHD after the clinical interview (FIG. 20). Note in FIG. 19 some patients presented because further evaluation wanted after previous ADHD diagnosis, or because evaluation sought for other disorders not ADHD. Some patients had general dissatisfaction with ADHD medications. In some, parents and teachers both ruled out ADHD (all scale scores <80th percentile). These results support that patients in this subgroup would be agreeable to the system result of recommendation for further testing.

In FIG. 20, note the initial impression recorded after user or clinician's unstructured interview of patient and parent (with blinding to EEG).

The OR results in FIGS. 11-20 show that there are statistically significant and clinically meaningful differences in ADHD patients with "EEG-no" (NEBA™: further testing, "FT") vs. ADHD patients with "EEG-yes" (NEBA™: confirmatory support, "CS"). ADHD patients with a system result of further testing are more likely to have conditions that would be of concern to an ADHD evaluation and/or could lead a clinician to exclude ADHD from primary diagnosis. If a user or clinician were to follow the system recommendation for further testing in accordance with an embodiment of the invention, he or she would likely find conditions that would be of concern to the ADHD evaluation. As such, the OR analyses support that the system result of further testing would be of benefit to the clinical evaluation.

It should be noted in the odds ratio (OR) comparisons, that the converse of the results for the "ADHD-yes/EEG-no" subgroup (NEBA™: further testing) is true for the "ADHD-yes/EEG-yes" subgroup (NEBA™: confirmatory support). In other words, ADHD patients with "EEG-yes" (NEBA™: confirmatory support) were less likely to have the complications that would warrant further testing. For instance, the "ADHD-yes/EEG-yes" subgroup was less likely to have had a history of problems with ADHD medications, less likely to be doing well academically and intellectually, and less likely to have expressed dissatisfaction with a previous or current ADHD diagnosis. The "ADHD-yes/EEG-yes" subgroup was less likely to have anger or aggression issues, uncorrected vision or hearing problems, a medical or neurological condition that could simulate ADHD, or a psychiatric disorder that could lead to ADHD exclusion from primary diagnosis. Further, when evaluating an individual of the "ADHD-yes/EEG-yes" subgroup (NEBA™: confirmatory support), the user or clinician would be more likely to have an initial impression of ADHD after the clinical interview. All of these OR results were statistically significant.

The results of analyses support that certain embodiments of the invention, such as use of the system 100 in FIG. 1, do succeed within the intended use. In summary, the system measure (e.g., EEG theta/beta ratio) can be reliably determined in children and adolescents who present to clinics with attention and behavior concerns (ICC=0.83 to 0.88). An ADHD patient with a system result of confirmatory support is likely to have ADHD as primary diagnosis (positive predictive value=94%). Confirmatory support by a biological assessment aid could be potentially beneficial in (1) helping to reduce the perceived stigma associated with ADHD and (2) helping the patient and parent to feel more comfortable with the clinician's diagnosis and treatment, which may in turn lead to improved compliance with the user or clinician's management of the disorder. An ADHD patient with a system result of a recommendation for further testing is likely to have complicating conditions that may be of concern to an ADHD evaluation and might lead the user or clinician to exclude ADHD from primary diagnosis (negative predictive value=80%; 9 significant OR results for complicating conditions). OR results showed that an ADHD patient with a system result of a recommendation for further testing was more likely to have the following complicating conditions that may be of concern to an ADHD evaluation and might lead a clinician to exclude ADHD from primary diagnosis: a psychiatric disorder that could lead to ADHD exclusion (OR=2), a medical or neurological condition that could simulate ADHD (OR=10), an uncorrected vision or hearing problem which could simulate ADHD (OR=2), history of adverse events (OR=9) or no improvement with ADHD medications (OR=4), primary concern of aggression (OR=2) or anger (OR=4), doing well academically and intellectually (OR=4), and dissatisfaction with a previous or current ADHD diagnosis (OR=8).

While the invention has been described in connection with what is presently considered to be the most practical of various embodiments, it is to be understood that the invention is not to be limited to the disclosed embodiments, but on the contrary, is intended to cover various modifications and equivalent arrangements included within the scope of the appended claims.

This written description uses examples to disclose embodiments of the invention, including the best mode, and also to enable any person skilled in the art to practice the invention, including making and using any devices or systems and performing any incorporated methods. The patentable scope of embodiments of the invention is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The claimed invention is:

1. A system for identifying a subgroup of attention deficit hyperactivity disorder (ADHD) patients at higher risk for complicating conditions, the system comprising:
   a data collection module operable to:
      receive, from a user or clinician, evaluation data associated with a plurality of patients identified with ADHD as a primary diagnosis; and
      obtain EEG data for each of the plurality of patients;
   a clinical/diagnostic module operable to:
      based at least in part on the EEG data, determine an indicator of ADHD, wherein the indicator supports a positive or negative ADHD evaluation; and
   a subgroup identification module operable to:
      correlate the indicator with the user's or clinician's evaluation data; and
      based at least in part on the correlation, determine at least one subgroup of the plurality of patients, wherein the correlation provides positive support for diagnosis of ADHD or provides support for further testing for complicating conditions before proceeding with diagnosis of ADHD in at least one patient within the at least one subgroup.

2. The system of claim 1, wherein determining at least one subgroup of the plurality of patients comprises determining a first subgroup receiving positive support, and a second subgroup receiving a recommendation for further testing.

3. The system of claim 2, wherein the at least one subgroup comprises a subgroup receiving a recommendation for further testing, and the subgroup identification module is further operable to:
   obtain further clinical data to determine whether one or more complicating conditions are present which could exclude ADHD as the primary diagnosis.

4. The system of claim 1, wherein the subgroup identification module is further operable to:
   provide a graded recommendation for any patients receiving support for further testing for complicating conditions before proceeding with diagnosis of ADHD.

5. The system of claim 1, wherein the EEG data comprises at least one theta/beta ratio calculation, or a ratio computed by dividing average percent power in the theta frequency band by average percent power in the beta frequency band.

6. The system of claim 1, wherein the correlation comprises a theta/beta ratio calculation within a predefined range, and wherein the correlation provides: (i) positive support for diagnosis of ADHD, (ii) a suggestion for further testing for complicating conditions before proceeding with diagnosis of ADHD or, (iii) a strong recommendation for further testing for complicating conditions before proceeding with diagnosis of ADHD in at least one patient within a predefined age range within the at least one subgroup.

7. The system of claim 1, further comprising:
   a report module operable to:
   output an indication for at least one patient within the at least one subgroup, wherein the indication corresponds to whether the correlation provides positive support for diagnosis of ADHD or provides support for further testing for complicating conditions before proceeding with diagnosis of ADHD in the at least one patient.

8. A computer program product, comprising a computer readable medium having computer readable code adapted to be executed to implement a method for identifying a subgroup of attention deficit hyperactivity disorder (ADHD) patients at higher risk for complicating conditions, the method comprising:
   receiving, from a user or clinician, evaluation data associated with a plurality of patients identified with ADHD as a primary diagnosis;
   obtaining, via the data collection module, EEG data for each of the plurality of patients;
   based at least in part on the EEG data, determining an indicator of ADHD via the clinical/diagnostic module, wherein the indicator supports a positive or negative ADHD evaluation;
   correlating the indicator with the user's or clinician's evaluation data; and
   based at least in part on the correlation, determining, via the subgroup identification module, at least one subgroup of the plurality of patients, wherein the correlation provides positive support for diagnosis of ADHD or provides support of further testing for complicating conditions before proceeding with diagnosis of ADHD in at least one patient within the at least one subgroup.

9. The computer program product of claim 8, wherein determining at least one subgroup of the plurality of patients comprises determining a first subgroup receiving positive support, and a second subgroup receiving a recommendation for further testing.

10. The computer program product of claim 9, wherein the at least one subgroup comprises a subgroup receiving a recommendation for further testing, and the method further comprises:
    obtaining further clinical data to determine whether one or more complicating conditions are present which could exclude ADHD as the primary diagnosis.

11. The computer program product of claim 8, wherein the method further comprises:
    providing, via the subgroup identification module, a graded recommendation for any patients receiving support for further testing for complicating conditions before proceeding with diagnosis of ADHD.

12. The computer program product of claim 8, wherein the EEG data comprises at least one theta/beta ratio calculation, or a ratio computed by dividing average percent power in the theta frequency band by average percent power in the beta frequency band.

13. The computer program product of claim 8, wherein the correlation comprises a theta/beta ratio calculation within a predefined range, and wherein the correlation provides: (i) positive support for diagnosis of ADHD, (ii) a suggestion for further testing for complicating conditions before proceeding with diagnosis of ADHD or, (iii) a strong recommendation for further testing for complicating conditions before proceeding with diagnosis of ADHD in at least one patient within a predefined age range within the at least one subgroup.

14. The computer program product of claim 8, wherein the method further comprises:
    outputting, via a report module, an indication for at least one patient within the at least one subgroup, wherein the indication corresponds to whether the correlation provides positive support for diagnosis of ADHD or provides support for further testing for complicating conditions before proceeding with diagnosis of ADHD in the at least one patient.

15. A computer-implemented method for identifying a subgroup of attention deficit hyperactivity disorder (ADHD) patients at risk for complicating conditions, the method comprising:
    using a data collection module, receiving, from a user or clinician, evaluation data associated with a plurality of patients identified with ADHD as a primary diagnosis; and obtaining EEG data for each of the plurality of patients;
using a clinical/diagnostic module, based at least in part on the EEG data, determining an indicator of ADHD, wherein the indicator supports a positive or negative ADHD evaluation; and
using a subgroup identification module, correlating the indicator with the user's or clinician's evaluation data; and
based at least in part on the correlation, determining at least one subgroup of the plurality of patients, wherein the correlation provides positive support for diagnosis of ADHD or provides support for further testing for complicating conditions before proceeding with diagnosis of ADHD in at least one patient within the at least one subgroup.

16. The method of claim 15, wherein the correlation comprises a theta/beta ratio calculation within a predefined range, and wherein the correlation provides: (i) positive support for diagnosis of ADHD, (ii) a suggestion for further testing for complicating conditions before proceeding with diagnosis of ADHD or, (iii) a strong recommendation for further testing for complicating conditions before proceeding with diagnosis of ADHD in at least one patient within a predefined age range within the at least one subgroup.

17. The method of claim 16, wherein the at least one subgroup comprises a subgroup receiving a recommendation for further testing, and the method further comprises:
obtaining further clinical data to determine whether one or more complicating conditions are present which could exclude ADHD as the primary diagnosis.

18. The method of claim 16, further comprising:
providing a graded recommendation for any patients receiving support for further testing for complicating conditions before proceeding with diagnosis of ADHD.

19. The method of claim 16, wherein the EEG data comprises either at least one theta/beta ratio calculation, or a ratio computed by dividing average percent power in the theta frequency band by average percent power in the beta frequency band.

20. The method of claim 16, further comprising:
outputting an indication for at least one patient within the at least one subgroup, wherein the indication corresponds to whether the correlation provides positive support for diagnosis of ADHD or provides support for further testing for complicating conditions before proceeding with diagnosis of ADHD in the at least one patient.

* * * * *